United States Patent [19]

Ruscoe et al.

[11] 4,194,001
[45] Mar. 18, 1980

[54] SYNERGISTIC INSECTICIDAL COMPOSITIONS

[75] Inventors: Colin N. E. Ruscoe, Braywick; Henry G. H. Alner, Wokingham; Brian C. Baldwin, Wargrave, all of England

[73] Assignee: Imperial Chemical Industries Limited, London, England

[21] Appl. No.: 828,826

[22] Filed: Aug. 29, 1977

[30] Foreign Application Priority Data

Sep. 6, 1976 [GB] United Kingdom ............... 36817/76

[51] Int. Cl.² .............................................. A01N 9/02
[52] U.S. Cl. ................................. 424/273 R; 424/304; 424/269; 424/305; 424/308
[58] Field of Search ............... 424/273, 304, 305, 306; 560/123, 124

[56] References Cited

U.S. PATENT DOCUMENTS

| | | | |
|---|---|---|---|
| 3,835,176 | 9/1974 | Matsuo et al. | 424/304 |
| 3,899,586 | 8/1975 | Okuno et al. | 424/306 |
| 3,973,036 | 8/1976 | Hirano et al. | 424/304 |
| 4,024,163 | 5/1977 | Elliott et al. | 260/347.4 |

FOREIGN PATENT DOCUMENTS 1148103 4/1969 United Kingdom .

Primary Examiner—V. D. Turner
Attorney, Agent, or Firm—Cushman, Darby & Cushman

[57] ABSTRACT

Synergized insecticidal and acaricidal compositions comprise a compound of Formula I wherein Y is H or CN, Z is phenyl, or 2,2-dichlorovinyl and R is (i) a group of Formula II where X is Cl or Br, or (ii) a group of Formula III where Q is CH₃ or Cl, in combination with 1-n-dodecylimidazole or 1-n-dodecyl-1,2,4-triazole.

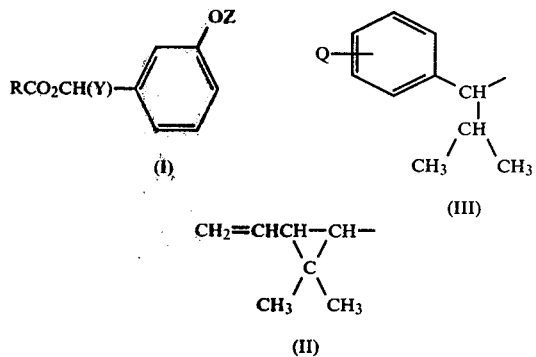

2 Claims, No Drawings

SYNERGISTIC INSECTICIDAL COMPOSITIONS

This invention relates to synergised insecticidal and acaricidal compositions and to methods of using them to combat insect and acarine pests.

British Pat. No. 1,148,103 disclosed the use of a class of imidazole derivatives, including 1-n-dodecylimidazole, as insecticide synergists for use with certain "prior art insecticides" (that is those known prior to the application date of the said British patent, viz. July 21, 1966).

We have now discovered that 1-n-dodecylimidazole and the related compound 1-n-dodecyl-1,2,4-triazole are especially effective synergists for certain insecticides not discovered until several years after the application date of the aforesaid British patent, and furthermore that compositions comprising these insecticides in combination with dodecylimidazole or dodecyltriazole have unexpected acaricidal properties.

Accordingly the present invention provides synergised insecticidal and acaricidal compositions comprising a compound of formula:

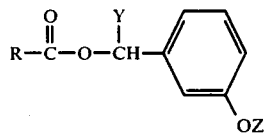

wherein Y is hydrogen or cyano, Z is phenyl or 2,2-dichlorovinyl, and R is (i) a group of formula:

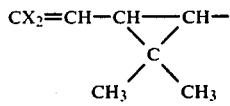

where X is chlorine or bromine, or (ii) a group of formula:

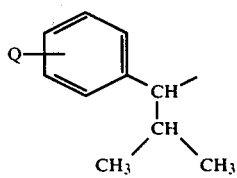

where Q is methyl or chlorine, in combination with a synergistically effective amount of a compound of formula:

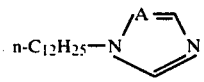

where A represents a nitrogen atom or a carbon atom bearing a hydrogen atom.

Compositions in which the synergist is 1-n-dodecylimidazole are especially preferred.

A particularly useful group of synergised compositions according the the invention are those comprising a compound of formula:

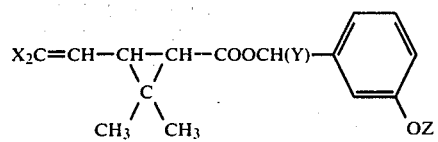

wherein each X is chlorine or bromine, Y is hydrogen or cyano and Z is phenyl or 2,2-dichlorovinyl, in combination with a synergistically effective amount of 1-n-dodecylimidazole.

The insect and acarine pests which may be combated with the invention compositions include those associated with agriculture (which term includes the growing of crops for food and fibre, horticulture and animal husbandry), forestry, the storage of products of vegetable origin, such as fruit, grain and timber, and also pests associated with the transmission of diseases of man and animals.

Preferred compounds of formula I above are those wherein X is chlorine or bromine, Y is hydrogen or cyano and Z is phenyl, including for example 3-phenoxybenzyl 3(2,2-dichlorovinyl)-2,2-dimethylcyclopropane carboxylate (hereinafter referred to as compound A) and α-cyano-3-phenoxybenzyl 3(2,2-dichlorovinyl)-2,2-dimethylcyclopropane carboxylate, and those wherein Q is chlorine, Y is cyano and Z is phenyl, for example, α-cyano-3-phenoxybenzyl 2-(4-chlorophenyl)-3-methylbutyrate.

The 1-n-dodecylimidazole or 1-n-dodecyl-1,2,4-triazole (hereinafter referred to as the synergist) may be present in the composition in an amount by weight greater or less than the amount of compound of formula I, but is preferably present in at least the same amount by weight as, and even more preferably in a greater amount than the compound of formula I. It is particularly preferred to have present about 5 to 50 parts by weight of the synergist for each part of the compound of formula I.

In other respects the compositions of the invention resemble conventional formulations for pesticidal usage, and in particular will usually comprise in addition to the compound of formula I and compound B an acceptable diluent or carrier material.

The composition may be in the form of dusting powders wherein the active ingredient and the synergist are mixed with a solid diluent or carrier, for example kaolin, bentonite, kieselguhr, or talc, or they may be in the form of granules, wherein the active ingredient and the synergist are absorbed in a porous granular material for example pumice.

Alternatively the compositions may be in the form of liquid preparations to be used as dips or sprays, which are generally aqueous dispersions or emulsions of the active ingredient and the synergist in the presence of one or more known wetting agents, dispersing agents or emulsifying agents.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient and the synergist in a suitable solvent, for example, a ketonic solvent such as diacetone alcohol, or an aromatic solvent such as trimethylbenzene, and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient and the synergist, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient and the synergist. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
 Aphis fabae (aphids)
 Megoura viceae (aphids)
 Aedes aegypti (mosquitoes)
 Dysdercus fasciatus (capsids)
 Musca domestica (houseflies)
 Pieris brassicae (white butterfly, larvae)
 Plutella maculipennis (diamond back moth, larvae)
 Phaedon cochleariae (mustard beetle)
 Telarius cinnabarinus (carmine spider mite)
 Aonidiella spp. (scale insects)
 Trialeuroides spp. (white flies)
 Blattella germanica (cockroaches)
 Spodoptera litteralia (cotton leaf worm)
 Chortiocetes terminifera (locusts)
 Lucilia sericata (blowflies)
 Boophilus microplus (ticks)

The compositions of the invention provide several benefits in use. Thus, although the synergist itself is devoid of any insecticidal or acaricidal activity, when it is used in combination with the compound of Formula I (hereinafter referred to as "the insecticide") in the synergised compositions of the invention it provides control of insect pests with lower rates of the insecticide than are required when the synergist is absent. Apart from this property of increasing insecticidal activity per se the presence of the synergist in the compositions also confers insecticidal activity against "resistant" strains of insects which in the absence of the synergist are substantially unaffected by application of the insecticide alone, because they have developed an ability to detoxify the insecticide through metabolism.

A further useful and unexpected advantage of the synergised compositions of the invention lies in their ability to provide useful control of acarine pests of plants. The compounds of Formula I when used without the synergist are very poor acaricides. If therefore, as frequently happens, a growing crop is infested with both insect pests and acarine pests, for example caterpillars and mites in cotton or top-fruit, then an insecticide and an acaricide must both be used to provide adequate control. However no separate acaricide is required when the synergised compositions of the invention are used, since the presence of the synergist, which is not acaricidal in its own right, confers acaricidal properties on the insecticide thus extending its spectrum of activity.

The compositions according to the invention may be prepared with the synergist and insecticidal ingredient both present and then transported to the site of application, or they may be prepared at or adjacent to the site of application as so-called "tank mixes" in which the synergist or a preformulated composition of the synergist is added directly to a preformulated composition of the insecticidal ingredient, and the mixture thus obtained immediately diluted with water to obtain a composition which is ready to apply to the crop or other locus of the pest by, for example, spraying. The advantage of using a tank mix is that it gives the user greater flexibility in choosing the ratio of synergist to insecticide to suit the particular host/pest situation involved.

In a further aspect therefore the invention provides a synergist composition suitable for admixture with an insecticidal composition, consisting of a compound of formula:

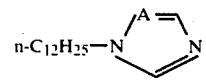

where A represents a nitrogen atom or a carbon atom bearing a hydrogen atom in association with one or more emulsifying agents and a diluent.

The emulsifying agents and diluents are preferably those to which reference has been made hereinabove in relation to the synergised insecticidal compositions of the invention, and indeed the synergist compositions are in general similar to the synergised insecticidal compositions described above, except of course that they do not contain an insecticidal ingredient. Examples of such preformulated compositions of the synergist are illustrated in Examples 1 to 3 herein.

Various aspects of the invention are illustrated in the following Examples. In Examples 6 to 10 Compound A is the insecticide permethrin (3-phenoxybenzyl (+)-cis/trans-3(2,2-dichlorovinyl)-2,2-dimethylcyclopropane carboxylate) and Compound B is 1-n-dodecylimidazole, and for these Examples compositions in the form of emulsifiable concentrates containing respectively 25% w/v of A alone, 25% w/v of B alone, 25% w/v of A with 25% w/v of 3, and 2.5% w/v of A with 25% w/v of B were prepared, and diluted with water to give the appropriate rate of A or B for use in the tests.

EXAMPLE 1

This Example illustrates a preformulated composition of 1-n-dodecylimidazole, in the form of an emulsifiable concentrate, suitable for preparing a tank mix with a composition of a compound of Formula I. It may be obtained by simply mixing together the following ingredients in the proportions given.

| Ingredients | % w/v |
| --- | --- |
| 1-n-Dodecylimidazole | 25.0 |
| 'Arylan' CA | 3.0 |
| 'Lubrol' N13 | 6.0 |
| 'Aromasol' H | to 100.0 |

('Arylan', 'Lubrol' and 'Aromasol' are Registered Trade Marks. 'Arylan' CA is calcium dodecylbenzene-sulphonate, 'Lubrol' NB is a condensate of nonylphenol with 13 molar proportions of ethylene oxide, and 'Aromasol' H is an aromatic solvent consisting principally of mixed trimethylbenzenes.)

EXAMPLE 2

This example illustrates another preformulated synergist composition which may be obtained by simply mixing the ingredients listed below in the proportions stated.

| Ingredients | % w/v |
| --- | --- |
| 1-n-Dodecylimidazole | 5.0 |
| 'Arylan' CA | 3.0 |
| 'Lubrol' N13 | 6.0 |
| 'Cerachlor' 65L | 20.0 |
| 'Aromasol' H | to 100.0 |

(Cerachlor' is a Registered Trade Mark. 'Cerachlor' 65L is a chlorinated liquid paraffinic hydrocarbon resin, containing about 65% chlorine by weight and having an average molecular weight of 460.)

EXAMPLE 3

By substitution of 1-n-dodecyl-1,2,4-triazole for 1-n-dodecylimidazole in the compositions of Examples 1 and 2 there may be obtained further preformulated compositions suitable for the preparation of tank mixes.

EXAMPLE 4

This Example illustrates a composition according to the invention, in the form of an emulsifiable concentrate obtained by mixing the listed ingredients in the proportions stated.

| Ingredients | % w/v |
| --- | --- |
| Permethrin | 5.0 |
| 1-n-dodecylimidazole | 25.0 |
| 'Arylan' CA | 3.0 |
| 'Lubrol' N13 | 6.0 |
| 'Aromasol' H | to 100.0 |

('Permethrin' is the accepted common name for the insecticide 3-phenoxybenzyl (+)-cis/trans-3(2,2-dichlorovinyl)-2,2-dimethyl-cyclopropane carboxylate.)

EXAMPLE 5

This Example illustrates the preparation of a tank mix. 100 parts by volume of a composition according to Example 1 is added to 10 parts by volume of a composition previously prepared by mixing together the following ingredients in the proportions stated.

| Ingredients | % w/v |
| --- | --- |
| Permethrin | 25.0 |
| 'Arylan' CA | 3.0 |
| 'Lissapol' NX | 20.0 |
| 'Aromasol' H | to 100.0 |

('Lissapol' is a Registered Trade Mark. 'Lissapol' NX is a condensate of nonylphenol with 9 molar proportions of ethylene oxide.)

This gives a mixture with a synergist to insecticide ratio of 10:1, which may be diluted with 1000 parts by volume of water to give a composition suitable for spraying in the control of insect and acarine pests of cotton.

EXAMPLE 6

Five adult cockroaches (*Blattella germanica*) were confined in a plastic beaker and sprayed with the composition under test (1.0 ml). The knockdown (KD) and % mortality were assessed after 4 and 24 hours respectively. The results are set out in the following Table.

| TREATMENT RATE (ppm) | | | |
| --- | --- | --- | --- |
| COMPOUND A | COMPOUND B | % KD | % MORTALITY |
| 25 | 0 | 100 | 100 |
| 25 | 250 | 100 | 100 |
| 10 | 0 | 100 | 78 |
| 10 | 100 | 100 | 100 |
| 5 | 0 | 44 | 33 |
| 5 | 50 | 100 | 100 |

EXAMPLE 7

10 Adult houseflies (*Musca domestica*) were confined in a plastic beaker and sprayed with the composition under test (1.0 ml). The knock-down (KD) was assessed after 4 hours and the mortality after 24 and 48 hours.

| TREATMENT RATE (ppm) | | | % MORTALITY | |
| --- | --- | --- | --- | --- |
| COMPOUND A | COMPOUND B | % KD | 24 HOURS | 48 HOURS |
| 50 | 0 | 100 | 90 | 100 |
| 50 | 50 | 100 | 100 | 100 |
| 50 | 500 | 100 | 100 | 100 |
| 25 | 0 | 100 | 65 | 100 |
| 25 | 25 | 100 | 100 | 100 |
| 25 | 250 | 100 | 100 | 100 |
| 10 | 0 | 100 | 20 | 40 |

-continued

| TREATMENT RATE (ppm) | | | % MORTALITY | |
|---|---|---|---|---|
| COMPOUND A | COMPOUND B | % KD | 24 HOURS | 48 HOURS |
| 10 | 10 | 100 | 15 | 50 |
| 10 | 100 | 100 | 95 | 100 |
| 5 | 0 | 45 | 0 | 0 |
| 5 | 5 | 100 | 20 | 75 |
| 5 | 50 | 100 | 15 | 65 |
| 2.5 | 0 | 40 | 0 | 10 |
| 2.5 | 2.5 | 100 | 5 | 60 |
| 2.5 | 25 | 100 | 5 | 30 |
| 1.25 | 0 | 0 | 0 | 0 |
| 1.25 | 1.25 | 85 | 0 | 45 |
| 1.25 | 12.5 | 100 | 5 | 30 |

EXAMPLE 8

Diamond backed moth caterpillars (*Plutella xylostella*) were kept in a dish with cabbage leaf as food and both the larvae and the food sprayed with the composition under test. The mortality was assessed 24 hours later and the results given in the following Table.

| TREATMENT RATE (ppm) | | |
|---|---|---|
| COMPOUND A | COMPOUND B | % MORTALITY |
| 2 | 0 | 90 |
| 2 | 2 | 100 |
| 2 | 20 | 100 |
| 1 | 0 | 41 |
| 1 | 1 | 63 |
| 1 | 10 | 97 |
| 0.5 | 0 | 0 |
| 0.5 | 0.5 | 37 |
| 0.5 | 5.0 | 77 |

EXAMPLE 9

Small French bean plants at the two leaf stage were infested with mites (*Tetranychus cinnibarinus*) and 24 hours later the adults on one leaf were removed leaving eggs deposited by the adults on that leaf. The leaves were then sprayed to drip point in a Potter tower with the composition under test. After 72 hours the mortality of the adult mites was assessed and after 168 hours the ovicidal effect was assessed.

The results are set out in the following Table.

| TREATMENT RATE (ppm) | | % MORTALITY | |
|---|---|---|---|
| COMPOUND A | COMPOUND B | ADULTS | EGGS |
| 50 | 0 | 0 | 0 |
| 0 | 100 | 0 | 0 |
| 50 | 100 | 100 | 100 |
| 25 | 50 | 30 | 0 |
| 12.5 | 50 | 20 | 0 |

It is a particularly surprising and unexpected finding that Compound A can be made effective against mites by the use of Compound B.

EXAMPLE 10

This Example illustrates the synergistic activity l-n-dodecyl-1,2,4-triazole. *Plutella xylostella* larvae were fed on cabbage leaves which had been previously sprayed to runoff with the composition under test. A composition containing 1.9 ppm of permethrin and 19 ppm of l-n-dodecyl-1,2,4-triazole gave a mortality after 72 hours of 47%, whereas a composition containing 1.9 ppm of permethrin alone gave a mortality after 72 hours of only 17%. A similar composition containing 19 ppm of l-n-dodecyl-1,2,4-triazole caused no mortality.

EXAMPLE 11

This Example illustrates the synergistic activity of l-n-dodecylimidazole with three insecticides, using a susceptible strain of cotton leaf worm (*Spodoptera littoralis*). Third instar larvae (half grown) were fed on cotton leaves treated with the compositions under test and the mortality assessed after 48 hours. The compounds were permethrin (I), cypermethrin (α-cyano-3-phenoxybenzyl (+)-cis/trans-3-(2,2-dichlorovinyl)-2,2-dimethylcyclopropane carboxylate (II) and phenvalerate (α-cyano-3-phenoxybenzyl 2-(4-chlorophenyl)-3-methylbutyrate (III). The results (expressed as % mortality) are given in the following table. The l-n-dodecylimidazole (B) was employed in a ratio of 10:1 by weight with respect to the insecticide.

| Insecticide | Rate (ppm) | Insecticide Alone % mortality | Insecticide + B % mortality |
|---|---|---|---|
| I | 31 | 27 | 60 |
| I | 15 | 13 | 33 |
| II | 15 | 60 | 86 |
| III | 62 | 60 | 86 |

EXAMPLE 12

This Example illustrates the synergistic activity of l-n-dodecylimidazole (B) with permethrin in the control of the locust *Chortiocetes terminifera*. The % mortality of second and third nymphal stages was assessed 24 hours after they had been directly sprayed with the compositions under test. The results are given in the following table.

| Rate (ppm) | Insecticide Alone % mortality | Insecticide + B % mortality |
|---|---|---|
| 400 | 52.2 | 99.7 |
| 200 | — | 99.8 |

We claim:

1. A synergised insecticidal and acaricidal composition comprises an insecticidally effective amount of an insecticide of the formula:

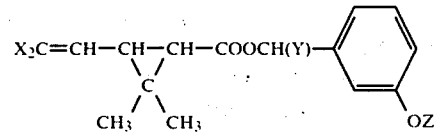

wherein each X is chlorine, Y is hydrogen and Z is phenyl, in combination with a synergistically effective amount of l-n dodecylimidazole in the range of about 5 to 50 parts of l-n-dodecylimidazole per part of said insecticide, the synergistic action of the l-n-dodecylimidazole being evidenced by the acaricidal activity added to the composition when the l-n-dodecylimidazole is used even though the l-n-dodecylimidazole is not itself an acaricide.

2. A method of combating insect or acarine pests at a locus which comprises treating the locus with a composition according to claim 1.

* * * * *